(12) United States Patent
Cannell et al.

(10) Patent No.: US 7,955,606 B2
(45) Date of Patent: Jun. 7, 2011

(54) AQUEOUS SYSTEMS CONTAINING POLYAMINE, SURFACTANT AND PHOSPHATE ESTER FOR WATER-INSOLUBLE MATERIALS

(75) Inventors: David W. Cannell, Plainfield, NJ (US); Hashimoto Sawa, Westfield, NJ (US); Nghi Van Nguyen, Edison, NJ (US)

(73) Assignee: L'Oreal, Paris (FR)

( * ) Notice: Subject to any disclaimer, the term of this patent is extended or adjusted under 35 U.S.C. 154(b) by 1176 days.

(21) Appl. No.: 11/583,284

(22) Filed: Oct. 19, 2006

(65) Prior Publication Data
US 2008/0095728 A1 Apr. 24, 2008

(51) Int. Cl.
*A61K 8/00* (2006.01)
*A61K 8/18* (2006.01)
*A61K 8/30* (2006.01)
*A61K 8/02* (2006.01)
*A61Q 5/00* (2006.01)
*A61Q 9/00* (2006.01)

(52) U.S. Cl. ............. 424/401; 424/70.1; 424/70.31

(58) Field of Classification Search ............ 424/401, 424/70.1, 70.31
See application file for complete search history.

(56) References Cited

U.S. PATENT DOCUMENTS

| 4,321,256 A | * | 3/1982 | Hasegawa et al. | 510/120 |
| 4,940,576 A | * | 7/1990 | Walsh | 424/70.11 |
| 2004/0045099 A1 | * | 3/2004 | Kuzuhara et al. | 8/405 |
| 2004/0076595 A1 | * | 4/2004 | Khan | 424/70.11 |

OTHER PUBLICATIONS

C.T.F.A. International Cosmetic Ingredient Dictionary and Handbook, 8$^{th}$ edition, vol. 2, (2000), pp. 1701 to 1703.
McCutcheon's "Detergents and Emulsifiers," North American Edition (1986), published by Allured Publishing Corporation, McCutcheon Division, MC Publishing Co., 175 Rock Road, Glen Rock, NJ 07452 USA.
McCutcheon's "Functional Materials," North American Edition (1992), McCutcheon Division, MC Publishing Co., 175 Rock Road, Glen Rock, NJ 07452 USA.

* cited by examiner

*Primary Examiner* — Johann R Richter
*Assistant Examiner* — Luke E Karpinski
(74) *Attorney, Agent, or Firm* — Connolly Bove Lodge & Hutz LLP

(57) ABSTRACT

The present invention is drawn to a aqueous composition containing: (a) at least one polyamine compound having at least three amino groups; (b) at least one nonionic surfactant; (c) at least one phosphate ester chosen from alkoxylated alkyl phosphate esters and alkyl phosphate esters; and (d) at least one water-insoluble material, and wherein the composition is both homogeneous, and clear to substantially clear in appearance.

26 Claims, No Drawings

AQUEOUS SYSTEMS CONTAINING POLYAMINE, SURFACTANT AND PHOSPHATE ESTER FOR WATER-INSOLUBLE MATERIALS

STATEMENT OF RELATED APPLICATIONS

Not applicable.

BACKGROUND OF THE INVENTION

The present invention relates to a novel aqueous system based on a combination of at least one polyamine compound having at least three amino groups, at least one nonionic surfactant, and at least one phosphate ester chosen from alkoxylated alkyl phosphate esters and alkyl phosphate esters, wherein the aqueous system allows water-insoluble materials to be incorporated into aqueous solutions.

Certain water-insoluble ingredients which are oftentimes desirable for the treatment of keratinous substrates are inherently difficult to incorporate into aqueous systems such as shampoos and conditioners without forming a traditional emulsion in either cream or lotion form. Moreover, many of these water-insoluble ingredients suppress lathering which makes the use of aqueous systems such as shampoos and body washes less desirable to consumers. Even in those aqueous systems which do employ these types of water-insoluble ingredients, their presence is minimal due to various performance drawbacks such as poor spreadability, foaming, removal and rinsing or, in the case of styling products, difficulties in removal via shampooing.

Also, when formulating clear aqueous delivery systems for use in treating keratinous substrates, water-insoluble compounds do not lend themselves to being used therein, due to their inability to significantly associate with the water present in the system.

Thus, there remains a need for an aqueous delivery system which can carry water-insoluble materials while remaining both homogeneous and clear to substantially clear in appearance.

BRIEF SUMMARY OF THE INVENTION

In order to achieve these and other advantages, the present invention is drawn to a aqueous composition containing:
(a) at least one polyamine compound having at least three amino groups;
(b) at least one nonionic surfactant;
(c) at least one phosphate ester chosen from alkoxylated alkyl phosphate esters and alkyl phosphate esters; and
(d) at least one water-insoluble material.

In another embodiment, the present invention is drawn to a process for treating a keratinous substrate by contacting the substrate with an aqueous composition containing:
(e) at least one polyamine compound having at least three amino groups;
(f) at least one nonionic surfactant;
(g) at least one phosphate ester chosen from alkoxylated alkyl phosphate esters and alkyl phosphate esters; and
(h) at least one water-insoluble material.

DETAILED DESCRIPTION OF THE INVENTION

Other than in the operating examples, or where otherwise indicated, all numbers expressing quantities of ingredients and/or reaction conditions are to be understood as being modified in all instances by the term "about".

The term "water-insoluble" means those compounds which are either completely or partially insoluble in water.

The term "carried" means that the aqueous delivery system containing the water-insoluble ingredients is both homogeneous and clear to substantially clear in appearance.

"At least one" as used herein means one or more and thus includes individual components as well as mixtures/combinations.

"Conditioning" as used herein means imparting to at least one keratinous fiber at least one property chosen from combability, manageability, moisture-retentivity, luster, shine, and softness. The state of conditioning is evaluated by measuring, and comparing, the ease of combability of the treated hair and of the untreated hair in terms of combing work (gm-in).

"Formed from," as used herein, means obtained from chemical reaction of, wherein "chemical reaction," includes spontaneous chemical reactions and induced chemical reactions. As used herein, the phrase "formed from", is open ended and does not limit the components of the composition to those listed, e.g., as component (i) and component (ii). Furthermore, the phrase "formed from" does not limit the order of adding components to the composition or require that the listed components (e.g., components (i) and (ii)) be added to the composition before any other components.

"Hydrocarbons," as used herein, include alkanes, alkenes, and alkynes, wherein the alkanes comprise at least one carbon, and the alkenes and alkynes each comprise at least two carbons; further wherein the hydrocarbons may be chosen from linear hydrocarbons, branched hydrocarbons, and cyclic hydrocarbons; further wherein the hydrocarbons may optionally be substituted; and further wherein the hydrocarbons may optionally further comprise at least one heteroatom intercalated in the hydrocarbon chain.

"Silicone compound," as used herein, includes, for example, silica, silanes, silazanes, siloxanes, and organosiloxanes; and refers to a compound comprising at least one silicon; wherein the silicone compound may be chosen from linear silicone compounds, branched silicone compounds, and cyclic silicone compounds; further wherein the silicone compound may optionally be substituted; and further wherein the silicone compound may optionally further comprise at least one heteroatom intercalated in the silicone chain, wherein the at least one heteroatom is different from the at least one silicon.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Keratinous substrate" as defined herein may be human keratinous fiber, and may be chosen from, for example, hair, eyelashes, and eyebrows, as well as the stratum corneum of the skin and nails.

"Polymers," as defined herein, include homopolymers and copolymers formed from at least two different types of monomers.

Advantageously, the aqueous composition of the present invention enables water-insoluble materials or ingredients to be carried by the composition and yet provide a clear to substantially clear appearance. Surprisingly, the use of an alcohol is not required in order to render the composition clear to substantially clear in appearance.

The composition of the invention is easy to formulate and gentle on the hair, skin, or eyelashes because the surfactants used therein are generally mild.

The composition of the present invention readily delivers water-insoluble ingredients to the targeted keratinous substrate. Accordingly, this composition can be used in the formulation of hair shampoos, conditioners, deep treatments, hair dyeing compositions, including oxidative dyes and bleaches, permanent waving compositions, curl relaxing compositions, hair setting compositions, bath and body products, sunscreens, cosmetics, skin moisturizers, and the like, all of which are homogeneous and clear to substantially clear in appearance.

The composition can also be used to deliver active water-insoluble pharmaceutical ingredients, particularly in topical applications. Such systems could further help protect against oxidation and rancidity by protecting sensitive ingredients in pharmaceuticals or foods.

The at least one polyamine compound of the present invention comprises at least three amino groups; preferably at least four amino groups; preferably at least five amino groups; preferably at least ten amino groups.

In one embodiment of the present invention, the at least one polyamine compound having at least three amino groups may, for example, be chosen from aminated polysaccharides comprising at least three amino groups, such as, for example, hydrolysates of aminated polysaccharides comprising at least three amino groups. In one embodiment, the at least one polyamine compound having at least three amino groups may, for example, be chosen from polymers. Suitable polymers for use as the at least one amine compound are polymers comprising at least three amino groups as defined herein. Non-limiting examples of suitable polymers include homopolymers comprising at least three amino groups, copolymers comprising at least three amino groups, and terpolymers comprising at least three amino groups. Thus, the at least one polyamine compound comprising at least three amino groups may be chosen from, for example, polymers comprising at least three amino groups formed from (i) at least one monomer unit comprising at least one amino group as defined herein, and, optionally, (ii) at least two additional monomer unit different from the at least one monomer (i); and polymers comprising at least three amino groups formed from (i) at least one monomer comprising at least three amino groups as defined herein, and, optionally, (ii) at least one additional monomer unit different from the at least three monomer (i). According to the present invention, the at least one additional monomer different from the at least one monomer (i) may or may not comprise at least one amino group as defined herein.

In one embodiment of the present invention, the at least one polyamine compound having at least three amino groups is chosen from polyamines. As used herein, "polyamines" comprise at least three repeating units, wherein each unit comprises at least one amino group as defined herein. In one embodiment, polyamines are chosen from polyethyleneimines. Polyethyleneimines suitable for use in the compositions of the present invention may optionally be substituted. Non-limiting examples of polyethyleneimines which may be used in the composition according to the present invention are the Lupasol™ products commercially available from BASF. Suitable examples of Lupasol™ polyethyleneimines include Lupasol™ PS, Lupasol PL, Lupasol™ PR8515, Lupasol™ G20, Lupasol™ G35 as well as Lupasol™ SC® Polyethyleneimine Reaction Products (such as Lupasol™ SC-61B®, Lupasol™ SC-62J®, and Lupasol™ SC-86X®). Other non-limiting examples of polyethyleneimines which may be used in the composition according to the present invention are the Epomin™ products commercially available from Aceto. Suitable examples of Epomin™ polyethyleneimines include Epomin™ SP-006, Epomin™ SP-012, Epomin™ SP-018, and Epomin™ P-1000.

Polyamines suitable for use in the present invention may also be chosen from polyvinylamines. Examples thereof include Lupamines® 9095, 9030, 9010, 5095, 1595 from BASF.

The polyamine compound having at least three amino groupss can also be substituted. An example of such a compound is PEG-15 Cocopolyamine from Cognis.

In another embodiment, the at least one polyamine compound comprising at least three amino groups is chosen from proteins and protein derivatives. Non-limiting examples of suitable proteins and protein derivatives for use in the present invention include those listed at pages 1701 to 1703 of the C.T.F.A. International Cosmetic Ingredient Dictionary and Handbook, $8^{th}$ edition, vol. 2, (2000). In one embodiment, the at least one polyamine compound comprising at least three amino groups is chosen from wheat protein, soy protein, oat protein, collagen, and keratin protein.

In one embodiment, the at least one polyamine compound comprising at least three amino groups is not chosen from proteins and protein derivatives. In one embodiment, the at least one polyamine compound comprising at least three amino groups is not chosen from compounds comprising lysine, compounds comprising arginine, and compounds comprising histidine. In one embodiment, the at least one polyamine compound comprising at least three amino groups is chosen from compounds comprising lysine, compounds comprising arginine, compounds comprising histidine, and compounds comprising hydroxylysine.

In the present invention, the at least one polyamine compound having at least three amino groups is preferably used in an amount of from greater than 0% to 30% by weight, preferably from greater than 0% to 10% by weight, and more preferably from greater than 0% to 5% by weight, based on the weight of the composition as a whole.

In general, nonionic surfactants having a Hydrophilic-Lipophilic Balance (HLB) of from 8 to 20, are contemplated for use by the present invention. Nonlimiting examples of non-ionic surfactants useful in the compositions of the present invention are disclosed in McCutcheon's "Detergents and Emulsifiers," North American Edition (1986), published by Allured Publishing Corporation; and McCutcheon's "Functional Materials," North American Edition (1992); both of which are incorporated by reference herein in their entirety.

Examples of nonionic surfactants useful herein include, but are not limited to, alkoxylated derivatives of the following: fatty alcohols, alkyl phenols, fatty acids, fatty acid esters and fatty acid amides, wherein the alkyl chain is in the $C_{12}$-$C_{50}$ range, preferably in the $C_{16}$-$C_{40}$ range, more preferably in the $C_{24}$ to $C_{40}$ range, and having from about 1 to about 110 alkoxy groups. The alkoxy groups are selected from the group consisting of $C_2$-$C_6$ oxides and their mixtures, with ethylene oxide, propylene oxide, and their mixtures being the preferred alkoxides. The alkyl chain may be linear, branched, saturated, or unsaturated. Of these alkoxylated non-ionic surfactants, the alkoxylated alcohols are preferred, and the ethoxylated alcohols and propoxylated alcohols are more preferred. The alkoxylated alcohols may be used alone or in mixtures thereof. The alkoxylated alcohols may also be used in mixtures with those alkoxylated materials disclosed herein-above.

Other representative examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) steareth-10 (a stearyl alcohol ethoxylate having an average degree of ethoxylation of 10), and steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding.

Also available commercially are Brij® nonionic surfactants from Uniqema, Willmington, Del. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij 72 (i.e., Steareth-2) and Brij 76 (i.e., Steareth-10).

Also useful herein as nonionic surfactants are alkyl glycosides, which are the condensation products of long chain alcohols, e.g. $C_8$-$C_{30}$ alcohols, with sugar or starch polymers. These compounds can be represented by the formula (S)n-O—R wherein S is a sugar moiety such as glucose, fructose, mannose, galactose, and the like; n is an integer of from about 1 to about 1000, and R is a $C_8$-$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a $C_8$-$C_{20}$ alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein are sucrose ester surfactants such as sucrose cocoate and sucrose laurate.

Other nonionic surfactants suitable for use in the present invention are glyceryl esters and polyglyceryl esters, including but not limited to, glyceryl monoesters, preferably glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of $C_{16}$-$C_{22}$ saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Uniqema, Wilmington, Del.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use herein are alkoxylated derivatives of glyceryl esters, sorbitan esters, and alkyl polyglycosides, wherein the alkoxy groups is selected from the group consisting of $C_2$-$C_6$ oxides and their mixtures, with ethoxylated or propoxylated derivatives of these materials being the preferred. Nonlimiting examples of commercially available ethoxylated materials include TWEEN® (ethoxylated sorbitan mono-, di- and/or tri-esters of $C_{12}$ to $C_{18}$ fatty acids with an average degree of ethoxylation of from about 2 to about 20).

Preferred nonionic surfactants are those formed from a fatty alcohol, a fatty acid, or a glyceride with a $C_4$ to $C_{36}$ carbon chain, preferably a $C_{12}$ to $C_{18}$ carbon chain, more preferably a $C_{16}$ to $C_{18}$ carbon chain, derivatized to yield an HLB of at least 8. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably greater than or equal to 8. Preferably the nonionic surfactants contain ethoxylate in a molar content of from 10-25, more preferably from 10-20 moles.

The nonionic surfactant will typically be present in the composition in an amount of from greater than 0% to 70% by weight, preferably from greater than 0% to 50% by weight, and more preferably from greater than 0% to 30% by weight, based on the weight of the composition as a whole.

The at least one phosphate ester chosen from alkoxylated alkyl phosphate esters and alkyl phosphate esters of the present invention may be chosen from a mono-ester corresponding to formula (I) and salts thereof:

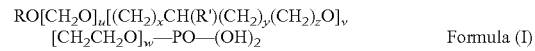    Formula (I)

a di-ester corresponding to formula (II) and salts thereof:

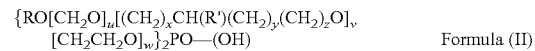    Formula (II)

a tri-ester corresponding to formula (III):

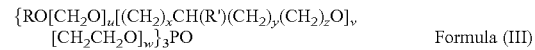    Formula (III)

and combinations thereof,
wherein:
R is a hydrocarbon radical containing from 6 to 40 carbon atoms;
u, v and w, independently of one another, represent numbers of from 0 to 60;
x, y and z, independently of one another, represent numbers of from 0 to 13;
R' represents hydrogen, alkyl, the sum of x+y+z being $\geq 0$.

The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formulas (I), (II) and (III),
R is linear or branched, acyclic or cyclic, saturated or unsaturated, aliphatic or aromatic, substituted or unsubstituted, preferably a linear or branched, acyclic $C_{6-40}$ alkyl or alkenyl group or a $C_{1-40}$ alkyl phenyl group, more particularly a $C_{8-22}$ alkyl or alkenyl group or a $C_{4-18}$ alkyl phenyl group, more preferably a $C_{12-18}$ alkyl group or alkenyl group or a $C_{6-16}$ alkyl phenyl group;

u, v, w, independently of one another, is preferably a number from 2 to 20, more preferably a number from 3 to 17 and most preferably a number from 5 to 15;

x, y, z, independently of one another, is preferably a number from 2 to 13, more preferably a number from 1 to 10 and most preferably a number from 0 to 8.

In general, the lower the number of carbon atoms in the R group of the phosphate ester, the more irritating to the skin and the less soluble in water the phosphate ester becomes. In contrast, the higher the number of carbon atoms in the R group, the milder to the skin and the thicker and more waxy the resultant product becomes. Accordingly, for best results, R should have from 12 to 18 carbon atoms.

The at least one phosphate ester chosen from alkoxylated alkyl phosphate esters and alkyl phosphate esters is present in the present composition in an amount of from greater than 0% to 30% by weight; greater than 0 to 15% by weight; greater than 0 to 5% by weight, based on the weight of the composition as a whole. Particularly preferred alkoxylated alkyl phosphate esters for use in the present invention are PPG-5-Ceteth-10 phosphate (CRODAFOS SG®), Oleth-3 phosphate (CRODAFOS N3 acid), Oleth-10 phosphate (CRODAFOS N10 acid), and a mixture of Ceteth-10 phosphate and Dicetyl phosphate (CRODAFOS CES) all sold by Croda, Particularly preferred alkyl phosphate esters are Cetyl phosphate (Hostaphat CC 100), Stearyl phosphate (Hostaphat CS 120) from Clariant.

It has surprisingly been found that by combining at least one polyamine compound, at least one nonionic surfactant, at least one phosphate ester, and at least one water-insoluble material, in a certain ratio by weight relative to each other, a homogeneous and clear to substantially clear aqueous composition can be formed capable of carrying up to about 50% by weight, preferably up to about 30% by weight, more preferably up to about 20% by weight, and most preferably up to about 10% by weight, all weights being based on the weight of the composition, of water-insoluble ingredients. The precise ratio by weight of polyamine compound:nonionic surfactant:phosphate ester:water-insoluble material necessary to make a clear to substantially clear composition will depend on the specific compounds chosen and, once chosen, can be determined by those of ordinary skill in the art.

Water-insoluble materials or ingredients include, but are not limited to, the following:

(1) Lipophilic "ingredients" or "materials" such as silicones, oil-soluble vitamins such as Vitamin E and Vitamin A, sunscreens, ceramides and natural oils: The lipophilic ingredients may be in the form of sunscreens, bacteriostats, moisturizers, colors, topical pharmaceuticals and the like. Preferred lipophilic ingredients include: Vitamin E, Vitamin E Acetate, Vitamin A Palmitate, olive oil, mineral oil, phytowax olive 6L25, 2-oleamido-1,3-octadecanediol, octylmethoxy cinnamate, octyl salicylate, and silicones such as phenyltrimethicone, dimethicone, cyclomethicone, phenyl trimethicone, dimethiconol, dimethicone copolyol, aminosilicone and laurylmethicone copolyol. The lipophilic ingredients will, for example, moisturize or condition the skin, hair, and/or eyelashes and leave behind no oily feel.

(2) Water-insoluble polymers, resins, and latexes, wherein the polymers and resins include but are not limited to those containing carboxyl moieties, such as acrylates and other carboxy polymers.

Preferred water-insoluble ingredients for use in the present invention include silicones ranging from low molecular weight fluids to high molecular weight gums; hydrocarbons such as mineral oil, petrolatum, paraffins, iso-paraffins, aromatic hydrocarbons, and the like; plant oils such as olive, avocado, coconut, and the like; fatty acids; fatty esters; fatty alcohols; and fatty waxes.

The composition can contain additional ingredients such as anionic surfactants, organic salts, inorganic salts, proteins, hair dyes, water-soluble polymers, quaternary ammonium compounds, complex and simple carbohydrates, amino acids, preservatives and fragrances.

The process for making the composition involves introducing at least one polyamine compound having at least three amino groups, at least one nonionic surfactant, at least one phosphate ester chosen from alkoxylated alkyl phosphate esters and alkyl phosphate esters, and at least one water-insoluble ingredient to an aqueous solution to form a diluted mixture. Heat may be optionally introduced at any stage of the preparation of the mixture and the final diluted mixture is allowed to cool. Preferably, the aqueous delivery system obtained can carry a high load (i.e., 50% is considered a high load) of the water-insoluble ingredient.

Another embodiment of the present invention is drawn to a process for treating a keratinous substrate comprising contacting the keratinous substrate with an aqueous composition containing:

(a) at least one polyamine compound having at least three amino groups;

(b) at least one nonionic surfactant;

(c) at least one phosphate ester chosen from alkoxylated alkyl phosphate esters and alkyl phosphate esters; and (d) at least one water-insoluble material.

The keratinous substrate includes but is not limited to, hair, skin, or eyelashes. The term treating in the context of this invention includes, but is not limited to, shampooing, conditioning, dyeing, bleaching, permanent waving, relaxing, setting, moisturizing, and making-up, for example, applying mascara or foundation.

As mentioned previously, the composition may be in the form of shampoos, conditioners (rinse-off and leave-in), deep treatments for hair, body washes, bath gels, hair dyeing compositions, permanent wave formulations, relaxers, make-up preparations, particularly mascara and foundation, and skin creams or lotions.

The composition may further contain proteins including hydrolyzed soy protein, lauryldimonium hydrolyzed soy protein (cationic Soya protein) and wheat amino acids. The proteins could also include corn, wheat, milk, or silk proteins, collagens, keratins, or others. Furthermore, taurine and arginine hydrochloride may be associated therein to maximize protein binding to the keratinous substrate. Cationic proteins or proteins in general may be stabilizers for the aqueous delivery system and enhance its delivery by changing the charge of the aqueous delivery system. The skin and the hair attract cationic ingredients, and proteins are generally substantive to these tissues.

Other optional ingredients include cationic polymers, such as polyquaternium 4, polyquaternium 6, polyquaternium 7, polyquaternium 10, polyquaternium 11, polyquaternium 16, polyquaternium 22, and polyquaternium 32, cationic conditioners, such as quaternium 27, behenamidopropyl PG-dimonium chloride, hydroxyethyl tallowdimonium chloride, hexadimethrine chloride, stearalkonium chloride, and cetrimonium chloride, isoparaffins, sodium chloride, propylene glycol, preservatives such as phenoxyethanol, methylparaben, ethylparaben, and propylparaben, pH adjusters such as phosphoric acid, humectants such as trehalose, and emollients such as octyldodecanol. Many other examples of materials from the classes listed above would be readily known to one of ordinary skill in the art.

Further, shampoos, conditioners, and deep treatments within the scope of the present invention, and which show significant substantivity for the hair, may be used on hair which has been treated, e.g., with color (dye or bleach) or chemicals (permanent wave or straightening), or which is dry or fine.

The invention will be further clarified by the following examples, which are intended to be illustrative of the invention, but not limiting thereof.

EXAMPLES

General Procedure: Heat water to 80° C. and all of the ingredients and mix well until uniform. Cool to RT, pour at 60° C. if necessary.

Example 1

The following mixtures A-G (in grams weight) were made using the General Procedure.

|  | A | B | C | D | E | F | G |
|---|---|---|---|---|---|---|---|
| D.I. Water | 64 | 64 | 64 | 64 | 64 | 64 | 64 |
| (PEI) (Polyethyleneimine) | 5 | 0 | 5 | 5 | 0 | 5 | 0 |
| Procetyl AWS | 25 | 25 | 0 | 25 | 25 | 0 | 0 |
| Crodafos SG | 2 | 2 | 2 | 0 | 0 | 0 | 2 |
| Olive Oil | 4 | 4 | 4 | 4 | 4 | 4 | 4 |
| Clarity | clear | hazy | hazy | hazy | hazy | hazy | hazy |
| Dilutions | clear | hazy | hazy | hazy | hazy | hazy | hazy |

The complete system, as shown in column A, is a clear system. It remains clear when diluted with water indefinitely. If one or two ingredients from the PNC mixture (PEI, Non-ionic, or Crodafos) are removed from the formula, as shown in columns B-G, the mixtures are no longer clear; they are hazy and remain hazy when diluted with water.

This example illustrates the necessity of having all three components (P, N, and C) in order for the system to carry olive oil, and to still remain clear upon dilution with water.

Example 2

The following PNC systems with vegetable oils were made using the General Procedure. All of the formulas below have been Q.S. to 100% with D.I. water. These systems contain Polyethyleneimine (PEI), Non-ionic (Procetyl AWS), Alkyl Ether Phosphates (Crodafos N3A, Crodafos N10A, and Crodafos SG) and oils (Olive oil, Avocado oil).

| PEI | Non-ionic | Crodafos | Vegetable Oil |
|---|---|---|---|
| PEI (10%) | Procetyl AWS (22%) | Crodafos N3A (2%) | Olive Oil (2%) |
| PEI (10%) | Procetyl AWS (30%) | Crodafos N10A (2%) | Olive Oil (4%) |
| PEI (10%) | Procetyl AWS (30%) | Crodafos SG (2%) | Olive Oil (4%) |
| PEI (10%) | Procetyl AWS (30%) | Crodafos N3A (2%) | Avocado Oil (4%) |
| PEI (10%) | Procetyl AWS (30%) | Crodafos N10A (2%) | Avocado Oil (4%) |
| PEI (10%) | Procetyl AWS (30%) | Crodafos SG (2%) | Avocado Oil (4%) |

These systems are clear, and remain clear when diluted with water indefinitely.

Example 3

The following PNC systems with silicones were made using the General Procedure. All of the formulas below have been Q.S. to 100% with D.I. water. These systems contain Polyethyleneimine (PEI), Non-ionic (Procetyl AWS), Alkyl Ether Phosphates (Crodafos N3A, Crodafos N10A, and Crodafos SG) and silicone (Phenyltrimethicone).

| PEI | Non-ionic | Crodafos | Silicone |
|---|---|---|---|
| PEI (10%) | Procetyl AWS (30%) | Crodafos N3A (1%) | Phenyltrimethicone (2%) |
| PEI (10%) | Procetyl AWS (30%) | Crodafos N10A (1%) | Phenyltrimethicone (2%) |
| PEI (10%) | Procetyl AWS (30%) | Crodafos SG (1%) | Phenyltrimethicone (2%) |

These systems are clear, and remain clear when diluted with water indefinitely.

Example 4

The following PNC systems with waxes were made using the General Procedure. All of the formulas below have been Q.S. to 100% with D.I. water. These systems contain Polyethyleneimine (PEI), Non-ionic (Procetyl AWS), Alkyl Ether Phosphates (Crodafos N3A, Crodafos N10A, and Crodafos SG) and wax (Phytowax Olive).

| PEI | Non-ionic | Crodafos | Wax |
|---|---|---|---|
| PEI (10%) | Procetyl AWS (30%) | Crodafos N3A (2%) | Phytowax Olive (4%) |
| PEI (10%) | Procetyl AWS (30%) | Crodafos N10A (2%) | Phytowax Olive (4%) |
| PEI (10%) | Procetyl AWS (30%) | Crodafos SG (2%) | Phytowax Olive (4%) |

These systems are clear, and remain clear when diluted with water indefinitely.

Example 5

The following PNC systems with hydrocarbons were made using the General Procedure. All of the formulas below have been Q.S. to 100% with D.I. water. These systems contain Polyethyleneimine (PEI), Non-ionic (Procetyl AWS), Alkyl Ether Phosphates (Crodafos N3A, Crodafos N10A, and Crodafos SG) and hydrocarbon (Mineral Oil).

| PEI | Non-ionic | Crodafos | Hydrocarbon |
|---|---|---|---|
| PEI (10%) | Procetyl AWS (30%) | Crodafos N3A (2%) | Mineral Oil (4%) |
| PEI (10%) | Procetyl AWS (30%) | Crodafos N10A (2%) | Mineral Oil (4%) |
| PEI (10%) | Procetyl AWS (30%) | Crodafos SG (2%) | Mineral Oil (4%) |

These systems are clear and remain clear when diluted with water indefinitely.

Example 6

The following PNC system with hydrocarbon was made using the General Procedure. The system contains Polyethyleneimine (PEI), Non-ionic (Procetyl AWS), Alkyl Ether Phosphate (Crodafos N3A) and hydrocarbon (Olive Oil).

| | |
|---|---|
| DI Water | 60.20% |
| PEI | 8.00% |
| Crodasfos N3A | 1.80% |
| Procetyl AWS | 25.00% |
| Mineral Oil | 5.00% |

Example 7

The following clear PNC system with hydrocarbon was made using the General Procedure. The system contains Polyethyleneimine (PEI), Non-ionic (Procetyl AWS), Alkyl Phosphate (Cetyl Phosphate) and hydrocarbon (Mineral Oil).

| | |
|---|---|
| DI Water | 67.80% |
| PEI | 0.10% |
| Cetyl Phosphate | 0.10% |
| Procetyl AWS | 30.00% |
| Mineral Oil | 2.00% |

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

What is claimed is:

1. A clear aqueous composition comprising:
   (a) at least one polyamine compound selected from the group consisting of polyethyleneimine, polyvinyl amine, and compounds comprising lysine, arginine, histidine, or hydroxy lysine;
   (b) at least one nonionic surfactant;
   (c) at least one phosphate ester selected from the group consisting of PPG-5-ceteth-10 phosphate, oleth-3 phosphate, oleth-10 phosphate, ceteth-10 phosphate, dicetyl phosphate, cetyl phosphate, stearyl phosphate, and mixtures thereof; and
   (d) at least one water-insoluble material.

2. The composition of claim 1 wherein (a) is polyethyleneimine.

3. The composition of claim 1 wherein (a) is polyvinylamine.

4. The composition of claim 1 wherein (a) is present in an amount of from about greater than 0 to about 30% by weight, based on the weight of the composition.

5. The composition of claim 1 wherein (a) is present in an amount of from greater than 0 to about 5% by weight, based on the weight of the composition.

6. The composition of claim 1 wherein (b) has an HLB of at least 8.

7. The composition of claim 1 wherein (b) is present in an amount of from greater than 0 to about 70% by weight, based on the weight of the composition.

8. The composition of claim 1 wherein (b) is present in an amount of from greater than 0 to about 30% by weight, based on the weight of the composition.

9. The composition of claim 1 wherein (c) is present in an amount of from greater than 0 to about 30% by weight, based on the weight of the composition.

10. The composition of claim 1 wherein (c) is present in an amount of from greater than 0 to about 5% by weight, based on the weight of the composition.

11. The composition of claim 1 wherein (d) is present in an amount of up to 50% by weight, based on the weight of the composition.

12. The composition of claim 1 wherein (d) is present in an amount of up to 10% by weight, based on the weight of the composition.

13. The composition of claim 1 wherein (d) is chosen from silicones, natural oils, synthetic oils, hydrocarbons, polymers, and mixtures, thereof.

14. A process for treating a keratinous substrate comprising contacting the keratinous substrate with the clear aqueous composition of claim 1.

15. The process of claim 14 wherein (a) is present in an amount of from greater than 0 to about 30% by weight, based on the weight of the composition.

16. The process of claim 14 wherein (a) is present in an amount of from greater than 0 to about 5% by weight, based on the weight of the composition.

17. The process of claim 14 wherein (b) has an HLB of at least 8.

18. The process of claim 14 wherein (b) is present in an amount of from greater than 0 to about 70% by weight, based on the weight of the composition.

19. The process of claim 14 wherein (b) is present in an amount of from greater than 0 to about 30% by weight, based on the weight of the composition.

20. The process of claim 14 wherein (c) is present in an amount of from greater than 0 to about 30% by weight, based on the weight of the composition.

21. The process of claim 14 wherein (c) is present in an amount of from greater than 0 to about 5% by weight, based on the weight of the composition.

22. The process of claim 14 wherein (d) is present in an amount of from greater than 0% to about 50% by weight, based on the weight of the composition.

23. The process of claim 14 wherein (d) is present in an amount of from greater than 0% to about 10% by weight, based on the weight of the composition.

24. The process of claim 14 wherein the keratinous substrate is hair.

25. The process of claim 14 wherein (d) is chosen from silicones, natural oils, synthetic oils, hydrocarbons, polymers, and mixtures, thereof.

26. A personal care composition comprising the composition of claim 1.

* * * * *